United States Patent [19]

Shioyama

[11] 4,399,307

[45] Aug. 16, 1983

[54] AMINATION PROCESS

[75] Inventor: Tod K. Shioyama, Bartlesville, Okla.

[73] Assignee: Phillips Petroleum Company, Bartlesville, Okla.

[21] Appl. No.: 357,121

[22] Filed: Mar. 11, 1982

[51] Int. Cl.$^3$ .................. C07C 87/40; C07C 87/50
[52] U.S. Cl. ................................. 564/437; 564/452; 203/57; 203/59; 203/69; 203/70
[58] Field of Search ............... 564/452, 437; 203/57, 203/59, 69, 70

[56] References Cited

U.S. PATENT DOCUMENTS

| | | | |
|---|---|---|---|
| 2,494,563 | 1/1950 | Kirk et al. | 564/452 |
| 2,606,924 | 8/1952 | Whitman | 564/452 |
| 3,283,002 | 11/1966 | Brake . | |
| 3,551,485 | 12/1970 | Ludwigshafen et al. . | |
| 3,676,495 | 7/1972 | Hoeschele | 564/452 |
| 4,293,687 | 10/1981 | Weissel et al. | 564/452 X |

FOREIGN PATENT DOCUMENTS 1019929 10/1964 United Kingdom .

*Primary Examiner*—Paul F. Shaver

[57] ABSTRACT

The distillation of 2,2'bis(4-aminocyclohexyl)propane to yield high purity product is effectively carried out using high boiling organic solvents.

7 Claims, No Drawings

AMINATION PROCESS

BACKGROUND

The diamine 2,2'-bis(4-aminocyclohexyl)propane (PACP) can be made by the reaction of ammonia and 2,2'-bis(4-hydroxycyclohexyl) propane (HBPA) over hydrogenation catalysts. PACP, in combination with diacids, is useful for the production of polyamides. Commercially available PACP supplies and crude amination reaction products contain organic impurities. Often these impurities are chemically and physically similar to the PACP, so that their separation from PACP is no simple matter.

THE INVENTION

The distillation of cyclic amines from certain solvents yields high purity compounds. Thus, in accordance with the present invention, the distillation of 2,2'-bis(4-aminocyclohexyl)propane using particular solvents yields a high purity compound. Compared to 54.8% recovery when no solvent is used, the distillation process of the invention can give 99.5% recovery of 99.9% pure product.

SOLVENTS

Operable solvents for use in the invention are inert hydrocarbons whose presence will not be detrimental to the distillation process. Suitable solvents include cyclic and acyclic aliphatic compounds, as well as aromatic and alkyl aromatic compounds. Typically, useful solvents are high boiling non-polar hydrocarbons.

By "high boiling" solvents is meant solvents boiling above at least 100° C., and preferably solvents boiling at about 140° C. or higher.

Exemplary solvents include octanes, decanes, dodecanes, tetradecanes, pentadecanes, hexadecanes, decahydronaphthalene, cyclohexylamine, xylenes, tetralin, and the like. Mixtures of solvents can be used.

The product purity and percent recovery of 2,2'-bis(4-aminocyclohexyl)propane (PACP) upon distillation is highly dependent on the purity of the initial pot charge. The addition of high boiling solvents tends to improve the separation of monoamine by-products, such as 2-phenyl-2'(4-aminocyclohexyl)propane, from the PACP. Only in pot charges where a significant amount (>5% or so) of monoamine impurities are present does the addition of high boiling solvent yield substantial improvements compared to straight distillation in the absence of solvent.

DISTILLATION PROCEDURE

Suitable distillation procedures are well-known. One preferred distillation technique is fractional distillation using a vacuum distillation apparatus.

Pot temperatures, while not critical, are generally dependent upon the apparatus used and the materials being treated. Useful temperatures include those from about 200° to 300° C., with those below 280° C. preferred.

Operable pressures are those at which distillation can be effectively carried out. While suitable pressures are readily discernible, typical pressures are no higher than 10 mm Hg, with about 1 to about 4 mm Hg preferred.

These and other distillation parameters can be determined by routine experimentation.

The ratio of crude PACP to solvent charged can vary over a wide range. Practical limits such as cost of added solvent, energy required for solvent recovery, and the degree of PACP recovery improvement may be controlling. Ratios of 10:1 to 1:10 are suitable, with 5:1 to 1:2 preferred, and about a 1:1 ratio most preferred.

CYCLIC AMINES

The amines which may be purified in accordance with the invention are amine-substituted compounds containing at least one cyclic moiety selected from saturated and unsaturated rings. Aromatic rings and cycloalkyl rings are among the cyclic groups contemplated. Useful cyclic compounds include aryl- and cycloalkyl-substituted compounds as well as alkyl-, alkenyl-, alkynyl-, and aryl-substituted cyclic compounds. Among the amines useful herein are bis(4-aminophenyl)methane, 2,2'-bis(3-aminophenyl)ethane, and bis(4-aminocyclohexyl)methane, with 2,2'-bis(4-aminocyclohexyl)propane being preferred.

PRODUCT UTILITY

The amines purified in accordance with the invention are useful as intermediates in the production of more complex materials. For example, 2,2'-bis(4-aminocyclohexyl)propane (PACP) is useful for the production of condensation polymers to be used in engineering plastics.

EXAMPLES

A number of distillations were carried out employing a variety of added solvents and PACP of varied initial purity. The results of these distillations are summarized in Table II. All distillations were carried out using a ½-inch diameter by 4-foot heated column packed with Penn State packing. This packing, also called Propak packing, consists of ¼" bent, rectangular stainless steel pieces with holes, curved into horseshoe shape. It can be obtained from Scientific Development Co., P.O. Box 795, State College, PA 16801. Individual reflux ratios and distillation pressures are indicated in Table II, as are the maximum distillation pot and distillation head temperatures. In general, pressures of 1–4 mm Hg with pot temperatures of 200°–280° C. and head temperatures of 145°–180° C. were employed.

The solvents investigated cover a wide range of boiling points and polarity, as Table I shows.

TABLE I

| Solvent | Boiling Point, °C. | Polarity, $E_T(30)$, Kcal/mol* |
|---|---|---|
| Sulfolane | 285 | 44.0 |
| N—methyl-2-pyrrolidinone | 202 | 42.2 |
| Diphenyl ether | 258 | 35.3 |
| Diphenyl sulfide | 296 | — |
| Pentadecane | 270 | 30.9** |
| Diethylene glycol dibutyl ether | 256 | 37.5*** |
| Soltrol 220≠ | 250–275 | 31.2, 30.9≠≠ |
| Cyclohexylamine | 134 | 33.3≠≠≠ |
| PACP | 325–330 (est.) | |

*From Angew. Chem. Int. Ed. Engl. 18, 98–110 (1979), derived from the longest-wavelength UV/VIS absorption band of negatively solvatochromic pyridiniophenolate at 25° C. and 1 bar.
**Value for n-hexane.
***Value for diethylene glycol diethyl ether.
≠Predominantly $C_{15}$ and $C_{16}$ branched, saturated hydrocarbons.
≠≠Values for cyclohexane and n-hexane.
≠≠≠Value for diisopropylamine.

TABLE II

| Solvent (g charged.) | Grams Crude PACP Charged | Reflux Ratio/Dist. Pressure/ Pot, Maximum Head Temps, °C. | PACP Purity Initial (Monoamine Content)* | Final | % Recovery |
| --- | --- | --- | --- | --- | --- |
| None | 116.5 | 3:1/1.0 mm Hg/248, 153 | 90.4 (9.2) | 99.4 | 54.8 |
| None | 735.0 | 2:1/4.0 mm Hg/295, 183 | 73.9 (26.1) | 99.5 | 58.9 |
| None | 245.0 | 3:1/1.5 mm Hg/255, 170 | 99.7 (≠) | 99.9 | 84.3 |
| Sulfolane (100.0) | 200.0 | 1:1/4.0 mg Hg/241, 173 | 93.9 (6.0) | 99.8 | 68.9 |
| Sulfolane (14.0) | 51.8 | 3:1/1.5 mm Hg/270, 163 | 80.5 (17.1) | 99.1 | 48.7 |
| Sulfolane (62.0) | 250.0 | 3:1/1.5 mm Hg/255, 170 | 99.7 (≠) | 99.9 | 79.6 |
| NMP** (82.5) | 82.5 | 3:1/1.0 mm Hg/240, 150 | 93.4 (2.6) | 99.4 | 55.8 |
| Diphenyl ether (84.0) | 84.0 | 3:1/1.0 mm Hg/235, 145 | 91.9 (6.5) | 98.9 | 64.6 |
| Diphenyl sulfide (100.0) | 97.4 | 3:1/1.0 mm Hg/237, 151 | 93.8 (4.3) | 98.9 | 36.0 |
| Pentadecane (93.0) | 91.0 | 3:1/1.0 mm Hg/245, 152 | 92.4 (6.5) | 99.9 | 99.5 |
| Pentadecane (30.0) | 60.0 | 1:1/1.0–1.5 mm Hg/225, 152 | 75.9 (22.6) | 97.4 | 80.2 |
| Pentadecane (37.0) | 112.0 | 3:1/2.0 mm Hg/280, 175 | 91.8 (6.8) | 99.3 | 81.4 |
| Pentadecane (63.0) | 250.0 | 3:1/1.5 mm Hg/250, 175 | 99.7 (≠) | 99.9 | 84.3 |
| DGE*** (93.0) | 93.0 | 3:1/2.0 mm Hg/250, 170 | 93.9 (4.1) | 99.9 | 83.7 |
| Soltrol 220 (125.0) | 249.0 | 2:1/2.0–2.5 mm Hg/255, 178 | 99.7 (≠) | 99.9 | 89.9 |
| Cyclohexylamine (102.5) | 185.1 | 2:1/2.5–3.0 mm Hg/208, 168 | 85.2 (13.1) | 98.4 | 73.4 |

*Impurity monoamines analyzed are: 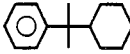 + 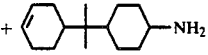

**N—methyl-2-pyrrolidinone
***Diethylene glycol dibutyl ether
≠Less than 0.05% (undetectable by HPLC)

The results summarized in Table II indicate that:

1. Solvent addition aids distillative recovery of PACP where significant amounts of monoamine analogs are present.

2. Relatively non-polar materials such as pentadecane are more effective than more polar solvents such as N-methyl-2-pyrrolidone or sulfolane for recovery of PACP.

3. PACP recovery is optimal when large amounts of added solvent are added. Note that a 1:1 PACP:pentadecane charge gives greater enhancement of PACP recovery than does a 2:1 PACP:pentadecane charge.

Reasonable variations, such as may occur to the skilled artisan, may be made in the invention without departing from the scope thereof.

I claim:

1. A process of recovering at least one high purity amine-substituted cyclic compound selected from the group consisting of bis(4-aminophenyl) methane, 2,2'-bis(3-aminophenyl) ethane, bis(4-aminocyclohexyl) methane, and 2,2'-bis(4-aminocyclohexyl) propane from a material containing such a compound in the presence of one or more monoamine homologs in quantities of about 5 percent or greater comprising (a) mixing at least one high boiling solvent with the material, and (b) distilling the mixture under suitable conditions to recover the amine-substituted compound.

2. The process of claim 1 wherein the solvent is selected from dodecane, tetradecane, pentadecane, hexadecane, decahydronaphthalene, tetrahydronaphthalene, and cyclohexylamine.

3. The process of claim 2 wherein the amine-substituted cyclic compound is 2,2'-bis(4-aminocyclohexyl)propane.

4. The process of claim 3 wherein the solvent is pentadecane.

5. The process of claim 4 wherein the ratio of 2,2'-bis(4-aminocyclohexyl)propane to solvent is within the range of about 10:1 to 1:10.

6. In a process for the fractional distillation of 2,2'-bis(4-aminocyclohexyl)propane from a solvent solution thereof, the improvement wherein the solvent is selected from the group consisting of dodecane, tetradecane, pentadecane, hexadecane, decahydronaphthalene, tetrahydronaphthalene, cyclohexylamine, and mixtures thereof.

7. The process of claim 6 wherein the solvent is pentadecane.